United States Patent
Weinstock et al.

(12) 
(10) Patent No.: US 6,458,845 B1
(45) Date of Patent: Oct. 1, 2002

(54) MACROPHAGE SCAVENGER RECEPTOR ANTAGONISTS

(75) Inventors: Joseph Weinstock, Wayne; Robert G. Franz, Plymouth Meeting; Dimitri E. Gaitanopoulos, Eagleville, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/018,457
(22) PCT Filed: Jun. 21, 2000
(86) PCT No.: PCT/US00/16988
§ 371 (c)(1),
(2), (4) Date: Dec. 12, 2001
(87) PCT Pub. No.: WO00/78145
PCT Pub. Date: Dec. 28, 2000

Related U.S. Application Data
(60) Provisional application No. 60/140,965, filed on Jun. 24, 1999.

(51) Int. Cl.$^7$ ................................................ A01N 41/06
(52) U.S. Cl. ........................ 514/604; 514/604; 514/605
(58) Field of Search ................................ 514/602, 603, 514/604, 605; 504/92, 90, 97

(56) References Cited

U.S. PATENT DOCUMENTS

| | | | |
|---|---|---|---|
| 3,357,977 A | 12/1967 | Errede | 260/244 |
| 4,334,011 A | 6/1982 | Aoki et al. | 430/552 |
| 4,454,225 A | 6/1984 | Sakai et al. | 430/505 |

*Primary Examiner*—Dwayne C. Jones
(74) *Attorney, Agent, or Firm*—Soma G. Simon; Mary E. McCarthy; Charles M. Kinzig

(57) ABSTRACT

Macrophage scavenger receptor antagonists are provided. Methods of treating cardiovascular disease comprising administration of the present compounds are also provided. The present compounds inhibit lipid accumulation within macrophage-derived foam cells.

5 Claims, No Drawings

MACROPHAGE SCAVENGER RECEPTOR ANTAGONISTS

This application is a 371 of PCT/US00/16988, filed on Jun. 21, 2000, which has priority to U.S. Provisional 60/140, 965, filed on Jun. 24, 1999.

FIELD OF INVENTION

Cardiovascular diseases are the leading cause of death in the U.S., accounting annually for more than one million deaths. Atherosclerosis is the major contributor to coronary heart disease and a primary cause of non-accidental death in Western societies. Since the prevention of atherosclerosis is an enormous unmet medical need, considerable effort has been made in defining the etiology and potential treatment of atherosclerosis and its consequences, including myocardial infarction, angina, organ failure and stroke. Despite this effort, there are many unanswered questions including how and when atherosclerotic lesions become life-threatening, the best point of intervention, and how to detect and monitor the progression of lesions.

There is widespread agreement that multiple risk factors contribute to atherosclerosis including hypertension, elevated total serum cholesterol, high levels of low density lipoprotein ("LDL") cholesterol, low levels of high density lipoprotein ("HDL") cholesterol, diabetes mellitus, severe obesity, and cigarette smoking. To date, treatment of atherosclerosis has been narrowly focused on treating elevated cholesterol levels and modifying lipids has become the major focus of treatment and research.

However, recent studies have indicated that 40% of deaths due to coronary disease occurred in men with total cholesterol levels of below 220 mg/dl. It is thus obvious that too great an emphasis is being placed on lipid lowering. Indeed, only 30% of patients with atherosclerosis have elevated lipid levels, indicating that other pathogenic factors are involved. A logical scenario for future therapies and preventive measures should therefore include a multidisciplinary approach consisting of diet modification, HMG-CoA reductase inhibition and novel therapies aimed directly at plaque growth and stability.

The initial lesion in atherosclerosis is the fatty streak, which arises from cholesteryl esters maintained as lipid droplets inside macrophage-derived foam cells. Macrophages down-regulate their LDL receptors and instead express mRNA and undergo new protein synthesis for a novel receptor for modified LDL. This receptor recognizes all modified forms of low-density lipoprotein and has come to be known as the macrophage scavenger receptor ("MSR"). If the macrophage is present in an environment that is continually generating modified LDL, it will accumulate lipid droplets of cholesteryl esters, continuing until the macrophage dies from its toxic lipid burden. The released lipid then forms the acellular necrotic core of the atherosclerotic lesion. Subsequent recruitment of fibroblasts, vascular smooth muscle cells and circulating monocytes and T-lymphocytes complete the inflammatory response and formation of the mature atherosclerotic plaque. Macrophage-derived foam cells are concentrated in the shoulders of plaques, where their secreted proteases and collagenases may contribute to plaque rupture which may lead to a fatal thrombotic event.

Plaque regression, a function of the dynamic balance among initiation, progression, stabilization and removal of plaque constituents, has been unequivocally demonstrated in humans as well as in numerous animal models. Multiple regression studies in non-human primates have shown that even relatively advanced lesions regress over time when atherogenic dietary stimuli are discontinued or pharmacological regimens are initiated.

Inhibition of lipid accumulation within macrophage-derived foam cells by utilizing MSR antagonists is expected to prevent plaque initiation, retard plaque progression, and initiate plaque regression through the process of "reversed cholesterol transport" to acceptor HDL. Thus, MSR antagonists provide a unique approach towards the pharmacotherapy of cardiovascular diseases such as atherosclerosis, coronary artery disease, renal disease, thrombosis, transient ischemia due to clotting, stroke, myocardial infarction, organ transplant, organ failure, and hypercholesterolemia.

SUMMARY OF THE INVENTION

The present invention involves sulfonamidobenzanilide compounds represented by Formula (I) hereinbelow and their use as macrophage scavenger receptor ("MSR") antagonists which are useful in the treatment of a variety of cardiovascular diseases including but not limited to atherosclerosis, coronary artery disease, renal disease, thrombosis, transient ischemia due to clotting, stroke, myocardial infarction, organ transplant, organ failure and hypercholesterolemia.

The present invention further provides methods for antagonizing the macrophage scavenger receptor in animals, including humans, comprising administering to an animal in need of treatment an effective amount of a compound of Formula (I), indicated hereinbelow.

The present invention further provides methods of inhibiting lipid accumulation within macrophage-derived foam cells.

DETAILED DESCRIPTION OF THE INVENTION

The compounds of the present invention are selected from Formula (I) hereinbelow:

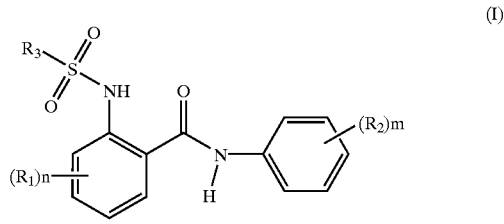

(I)

wherein:

$R_1$, and $R_2$ are independently selected from the group consisting of hydrogen, alkyl, alkenyl, arylalkyl, acyl, aroyl, haloalkyl, halo, carboxy, carboalkoxy, carbamyl, alkylcarbamyl, arylcarbamyl, cyano, alkoxy, hydroxyl, phenylazo, amino, nitro, alkylamino, arylamino, arylalkylamino, acylamino, aroylamino, alkylthio, arylalkylthio, arylthio, alkysulfinyl, arylsulfinyl, arylalkylsulfinyl, alkylsulfonyl, arylsulfonyl, arylalkylsulfonyl, sulfamyl, arylsulfonamido, and alkylsulfonamido;

or the $R_1$ moiety represents a fused ring forming a benzothiophene, naphthalene, quinoline, or isoquinoline with the ring it substitutes;

or $(R_1)_n$ and the ring it substitutes represents a heterocycle selected from the group consisting of thiophene, furan, pyridine, pyrimidine, and pyrazine, and benzo analogs thereof; and R₃ is independently selected from the group consisting of alkyl, haloalkyl, R₁ aryl and R₁ aralkyl, and R₁ substituted heterocycles selected from the group consisting of thiophene, furan, pyridine, pyrimidine, pyrazine, imidazole, and thiazole, and benzo analogs thereof;

or R₃ and the ring it substitutes represents a R₁ substituted heterocycle selected from the group consisting of thiophene, furan, pyridine, pyrimidine, and pyrazine, and benzo analogs thereof.

As used herein, "alkyl" refers to an optionally substituted hydrocarbon group joined together by single carbon-carbon bonds. Preferred alkyl substituents are as indicated throughout. The alkyl hydrocarbon group may be linear, branched or cyclic, saturated or unsaturated.

As used herein, "aryl" refers to an optionally substituted aromatic group with at least one ring having a conjugated pi-electron system, containing up to two conjugated or fused ring systems. "Aryl" includes carbocyclic aryl, heterocyclic aryl and biaryl groups, all of which may be optionally substituted. Preferred aryl substituents are as indicated throughout.

The compounds of the present invention may contain one or more asymmetric carbon atoms and may exist in racemic or optically active forms. All of these compounds and diastereomers are, contemplated to be within the scope of the present invention.

Preferred compounds of the present invention are selected from the group consisting of:

N-Phenyl-2-(3-trifluoromethylphenylsulfonamido)benzamide,

5-Bromo-N-(3,4-dichlorophenyl)-2-(3-trifluoromethylphenylsulfonamido)benzamide,

N-(4-Chlorophenyl)-2-(2-fluorophenylsulfonamido)benzamide,

5-Bromo-N-(3-trifluoromethylphenyl)-2-(5-chloro-2-thienylsulfonamido)benzamide,

5-Chloro-N-(4-chlorophenyl)-2-(5-chloro-2-thienylsulfonamido)benzamide,

N-(3-Chloro-4-methoxyphenyl)-2-(4-methoxyphenylsulfonamido)benzamide,

N-Phenyl-2-(2-fluorophenylsulfonamido)benzamide,

N-(4-Chlorophenyl-2-(3-trifluoromethylphenylsulfonamido)benzamide,

N-Phenyl-2-(4-methoxyphenylsulfonamido)benzamide,

N-(4-Chlorophenyl-2-(3-trifluoromethylphenylsulfonamido)-4-methoxybenzamide,

N-(3-Chloro-4-methoxyphenyl-2-(3-trifluoromethylphenylsulfonamido)-4-methoxybenzamide, N-(3,4-Dichlorophenyl)-2-(2-fluorophenylsulfonamido)-5-methoxybenzamide, N-(4-chlorophenyl)-2-(3-trifluoromethylphenylsulfonamido)-5-methoxybenzamide, 5-Chloro-N-(4-chlorophenyl)-2-(4-chlorophenylsulfonamido)benzamide, 5-Chloro-N-(4-chlorophenyl)-2-(3,3,3-trinfluoroethylsulfonamido)benzamide, N-(3,4-Dichlorophenyl)-2-(phenylsulfonamido)-5-methoxybenzamide, 2-(4-Chlorophenylsulfonamido)-N-(4-ethoxycarbonylphenyl)benzamide, 5-Bromo-N-phenyl-2-(2-fluorophenylsulfonamido)benzamide;

5-Bromo-N-phenyl-2-phenylsulfonamido)benzamide;

5-Bromo-N-phenyl-2-(5-chloro-2-thienylsulfonamido)benzamide;

5-Bromo-N-(4-chlorophenyl-2-(5-chloro-2-thienylsulfonamido)benzamide;

5-Bromo-N-phenyl-2-(4-methoxyphenylsulfonamido)benzamide;

5-Bromo-N-(4chlorophenyl)-2-(2-fluorophenylsulfonamido)benzamide;

5-Bromo-N-(4-Bromophenyl)-2-(4-nitrophenylsulfonamido)benzamide;

5-Bromo-N-(4-Bromophenyl)-2-(5-dimethylamino-1-naphthylsulfonamido)benzamide;

5-Bromo-N-(4-Bromophenyl)-2-(phenylsulfonamido)benzamide;

5-Bromo-N-(4-Bromophenyl)-2-(3,4-difuorophenylsulfonamido)benzamide;

5-Bromo-N-(4-Bromophenyl)-2-(3-trifluoromethylphenylsulfonamido)benzamide;

5-Bromo-N-(4-Bromophenyl)-2-(n-butylsulfonamido)benzamide;

5-Bromo-N-(4-Bromophenyl)-2-(benzylsulfonamido)benzamide;

5-Bromo-N-(4-Bromophenyl)-2-(8-isoquinolylsulfonamido)benzamide;

5-Bromo-N-(4-Bromophenyl)-2-(2-fluorophenylsulfonamido)benzamide;

5-Bromo-N-(4-Bromophenyl)-2-(2,1,3-benzothiadiazol-4-ylsulfonamido)benzamide;

5-Bromo-N-(4-Bromophenyl)-2-(4-chlorophenylsulfonamido)benzamide;

5-Bromo-N-(4-Bromophenyl)-2-(3-chloro-4-fluorophenylsulfonamido)benzamide;

5-Bromo-N-(4-Bromophenyl)-2-(3-chloro-2-methylphenylsulfonamido)benzamide; and

5-Bromo-N-(4-Bromophenyl)-2-(2,4,6-trimethylphenylsulfonamido)benzamide;

5-Bromo-N-(4-Bromophenyl)-2-(4-iodophenylsulfonamido)benzamide;

5-Bromo-N-(4-Bromophenyl)-2-(3-chloropropylsulfonamido)benzamide;

N-(4-Bromophenyl)-5-chloro-2-(4-trifluoromethoxyphenyl)benzamide;

5-Bromo-N-(3-trifluoromethylphenyl)-2-(3-trifluoromethylphenylsulfonamido)benzamide;

5-Bromo-N-(4-Bromophenyl)-2-(4-chorophenylsulfonamido)benzamide;

5-Bromo-N-(4-Bromophenyl)-2-(3-chloro-4-fluorophenylsulfonamido)benzamide;

5-Bromo-N-(4-Bromophenyl)-2-(3-chloro-2-methylphenylsulfonamido)benzamide;

5-Bromo-N-(4-Bromophenyl)-2-(2,4,6-trimethylphenylsulfonamido)benzamide;

5-Bromo-N-(4-Bromophenyl)-2-(2-fluorophenylsulfonamido)benzamide;

5-Bromo-N-(4-Bromophenyl)-2-(3,4-dimethoxyphenylsulfonamido)benzamide;

5-Bromo-N-(4-Bromophenyl)-2-(4-phenylazophenylsulfonamido)benzamide;

5-Bromo-N-(4-Bromophenyl)-2-(4-trifluoromethylphenylsulfonamido)benzamide;

5-Bromo-N-(4-Bromophenyl)-2-(2-methylphenylsulfonamido)benzamide;

5-Bromo-N-(4-Bromophenyl)-2-(phenylsulfonamido)benzamide;

5-Bromo-N-(4-Bromophenyl)-2-(2-naphthylsulfonamido)benzamide;

5-Bromo-N-(4-Bromophenyl)-2-(4-phenylphenysulfonamido)benzamide;

5-Bromo-N-(4-Bromophenyl)-2-(3-chloropropylsulfonamido)benzamide;

5-Bromo-N-(4-Bromophenyl)-2-(2-phenylvinyl)benzamide;

5-Bromo-N-(4-Bromophenyl)-2-(4-iodophenylsulfonamido)benzamide; and

5-Bromo-N-(4-Bromophenyl)-2-(4-t-butylphenylsulfonamido)benzamide.

Most preferred compounds of the present invention are selected from the group consisting of:

5-Bromo-N-(4-Bromophenyl)-2-(4-chlorophenylsulfonamido)benzamide;

5-Bromo-N-(4-Bromophenyl)-2-(3-chloro-4-fluorophenylsulfonamido)benzamide;

5-Bromo-N-(4-Bromophenyl)-2-(3-chloro-2-methylphenylsulfonamido)benzamide; and

5-Bromo-N-(4-Bromophenyl)-2-(2,4,6-trimethylphenylsulfonamido)benzamide.

Pharmaceutically acceptable salts for use when basic groups are present include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present.

The present invention provides compounds of Formula (I) above which can be prepared using standard techniques. An overall strategy for preparing preferred compounds described herein can be carried out as described in this section. The examples which follow illustrate the synthesis of specific compounds. Using the protocols described herein as a model, one of ordinary skill in the art can readily produce other compounds of the present invention.

Scheme 1

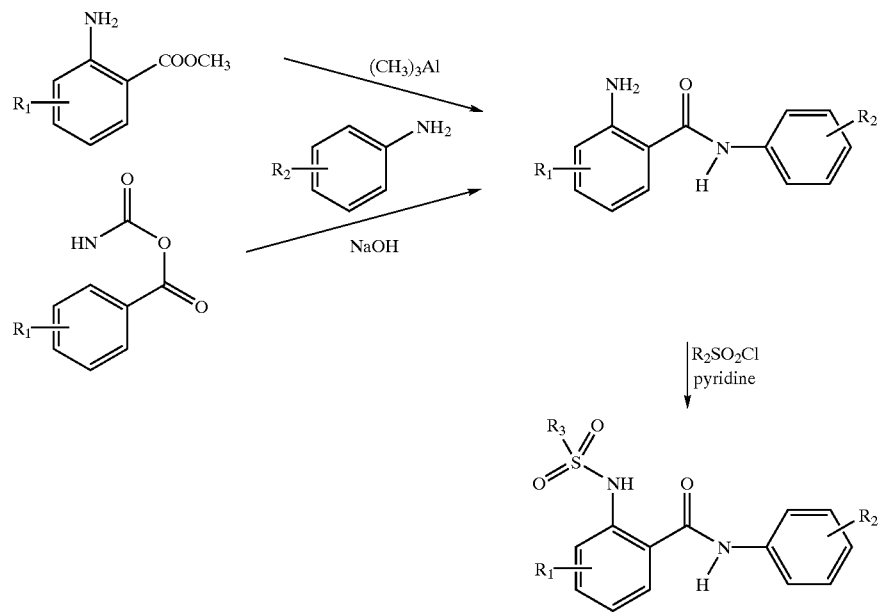

Scheme 2

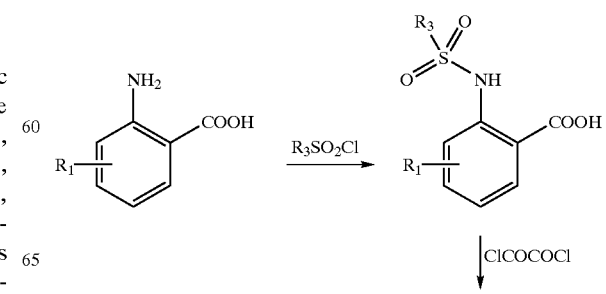

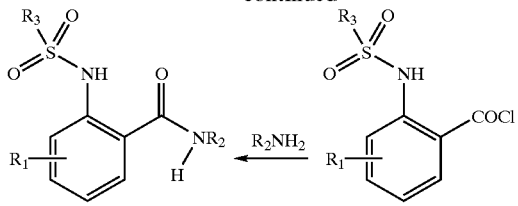

EXAMPLE 1

N-(4-Bromophenyl)-2-amino-5-bromobenzamide

A 11.6 ml portion of a 2.0 M solution of trimethylaluminum (23.2 mmol) was added to a solution of 4.0 g (23.25 mmol) of 4-bromoaniline at 0° C. The reaction mixture was held at ambient temperature for 45 min. and then cooled to 0° C. Methyl 2-amino-5-bromobenzoate (4.72 g, 23.25 mmol) was added in small portions, and after a vigorous gas evolution ceased the reaction mixture was held at ambient temperature for 18 hr. The reaction mixture was then poured into 250 ml of 10% HCl (further gas evolution occurred) and the solid which formed collected by filtration. The solid was washed in turn with water and toluene and then dried at room temperature. TLC silica, $CHCl_3$:MeOH 9:1 with a drop of formic acid, $R_f$ 0.80–0.90 and NMR identical with that of an authentic sample. This is a general procedure which works with a wide variety of aromatic and heteroaromatic anthranilic acid and aniline analogs.

A mixture of 12.1 g (50 mmol) of 5-bromoisatoic anhydride, 9.4 g (55 mmol) of 4-bromoaniline, and 0.2 g (5 mmol) of NaOH in 150 ml of dioxane was refluxed for 18 hr. The cooled reaction mixture was filtered and concentrated under vacuum. The residue crystallized on addition of 95% EtOH. The solid was collected by filtration and washed with ethanol. A sample purified by thick layer chromatography (silica, 15% EtOAc in hexane) gave the expected NMR, MS, and elemental analysis.

A similar procedure starting from 5-chloroisatoic anhydride and 4-bromoaniline gave N-(4-bromophenyl)-2-amino-5-chlorobenzamide which gave the expected NMR, MS, and elemental analysis.

EXAMPLE 2

5-Bromo-N-(4-Bromophenyl)-2-(4-chlorophenylsulfonylamino)benzamide

A solution of N-(4-Bromophenyl)-2-amino-5-bromobenzamide (8.64 g, 23.3 mmol), 4-chlorobenzenesulfonyl chloride (4.98 g, 23.6 mmol), and 7.37 g (93.2 mmol) in 300 ml of $CH_2Cl_2$ was allowed to stand at room temperature for 2 days. The reaction mixture was concentrated under vacuum and the residue dissolved in EtOAc. The solution was washed twice with 10% HCl, water, 5% $NaHCO_3$, water, and dried over $MgSO_4$. Concentration and recrystallization from 10% EtOAc in hexane gave product which had satisfactory NMR, MS, and elemental analysis.

EXAMPLE 3

5-Bromo-N-(4-Bromophenyl)-2-(4-bromophenylsulfonylamino)benzamide

A solution of 31.5 mg (85 µmol) of N-(4-Bromophenyl)-2-amino-5-bromobenzamide, 32.5 mg (127.5 µmol) of 4-bromobenzenesulfonyl chloride, and 28 µl (340 µmol) of pyridine in 1 ml of $CH_2Cl_2$ was agitated for 18 hr. Then 84.5 mg (382 µmol) of polyamine resin HL (Nova Biochem, 4.53 mmol/g) was added, the mixture agitated for 18 hr, and the solids removed by filtration. Concentration under vacuum and purification by preparative HPLC (C18, 20–95% acetonitrile—0.1% aqueous TFA) gave product which gave a satisfactory HPLC-MS analysis.

Using procedures similar to those in Examples 2 and 3, the products from reaction of 5-bromo-N-(4-bromophenyl)-2-(4-chlorophenylsulfonylamino)benzamide with the following sulfonyl chlorides were obtained: 3-chlorophenyl-, 4-chlorophenyl-, 3,4-dichlorophenyl-, 3-chloro-4-fluoro-, 2-fluorophenyl-, 2,5-dimethoxyphenyl-, 3,4-dimethoxyphenyl-, 4-n-butoxyphenyl-, 2-trifluoromethylphenyl-, 4-phenylazophenyl-, 4-trifluoromethylphenyl-, 3,5-bis-trifluoromethylphenyl-, 2-methylphenyl-, 2,4,6-trimethylphenyl-, 2-naphthyl-, methane-, trifluoromethane-, 2-thienyl-, 5-chloro-2-thienyl-, 4-biphenylyl-, 3-chloropropyl-, 4-cyanophenyl-, 3,5-dichlorophenyl-, styryl-, 2-methoxycarbonyl-3-thienyl-, 4-iodophenyl-, 2,6-dichlorophenyl-, 4-t-butylphenyl-, and 2,2,2-trifluoroethyl-. The products gave satisfactory results on HPLC-MS analyses.

EXAMPLE 4

N-(3-Chloro-4-methoxyphenyl)-2-(4-methylphenylsulfonylamino)benzamide

A solution of 3.45 g (25 mmol) of sodium carbonate and 1.0 g (7.3 mmol) of anthranilic acid in 50 ml of water at 60° was treated with 2.09 g (10.95 mmol) of p-toluenesulfonyl chloride and held at 70° for 30 min. The reaction mixture was cooled to ambient temperature and acidified with 10% HCl. After standing for 18 hr the product was collected by filtration, washed with water and dried to give N-4-methylphenylsulfonylanthranilic acid as a solid, mp 226–229°.

A suspension of 0.5 g (1.7 mmol) of this acid in 25 ml of methylene chloride was treated with 1.09 g (8.6 mmol) of oxalyl chloride and 1 drop of DMF. After 4.5 hr 50 ml of toluene was added and then concentrated under vacuum. The residue was dissolved in 50 ml of toluene and treated with a mixture of 3-chloro-p-anisidine (0.33 g (1.89 mmol) and ) 8 g (8 mmol) of triethylamine and allowed to stand for 18 hr. The reaction mixture was diluted with dilute HCl and the solids collected by filtration and washed with water and toluene to give the expected product as crystals, mp 181–182° C., soften 173° C.

This procedure could be used to give a variety of N-substituted benzamides starting from a common N-sulfonylanthranilic acid and a variety of amines.

With appropriate manipulation and protection of any chemical functionality, synthesis of the remaining compounds of Formula (I) is accomplished by methods analogous to those above and to those described in the Experimental section.

In order to use a compound of Formula (I) or a pharmaceutically acceptable salt thereof for the treatment of humans and other mammals, it is normally formulated in accordance with standard pharmaceutical practice as a pharmaceutical composition.

The present compounds can be administered by different routes including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous. For injection, the compounds of the invention are formulated inliquid solutions, preferably, in physiologically compatible buffers or solutions, such as saline solution, Hank's solution, or Ringer's solution. In addition, the compounds may be formulated in solid form and re-dissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various compounds to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula (I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease.

The MSR receptors described in the present application belong to a recently classified group designated the SR-A group and exist in two forms, type A-I and type A-II, which arise through differential exon splicing of a single gene. The terms "MSR" and "SR-A" are used interchangeably in the present application.

Diseases and disorders which might be treated or prevented, based upon the affected cells, include atherosclerosis, coronary artery disease, renal disease, thrombosis, transient ischemia during clotting, stroke, organ transplant, organ failure, myocardial infarction and hypercholesterolemia.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs, Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (I) are demonstrated by the following tests.

Assays of MSR activity, both degradation and binding/internalization, were adapted from Goldstein et al., "Receptor-mediated Endocytosis of Low-density Lipoprotein in cultured Cells," Methods Enzymol., 98:241–260 (1983); incorporated herein in its entirety by reference. Briefly, 293 cells transfected with MSRI or II are seeded at $10^5$ cells/ml/well in a 24-well dish in Eagle's Minimal Essential Medium. with 2 mM glutamine, 10% FCS and 0.4 mg/ml geneticin. After 2 days, the medium is replaced with 500 µl fresh serum-free medium containing 2 mg/ml BSA and 125[I]-AcLDL (iodinated acetylated low density lipoprotein) at 5 µg/ml, and cells are incubated at 37C for 5 hours. After this suitable period for ligand degradation, cells are removed to a 4C cold room. Supernatant is removed into trichloroacetic acid, and the mixture is centrifuged. The supernatant is chloroforn-extracted in order to isolate 125 [I]-monoiodotyrosine, the degradation product of 125[I]-AcLDL, and portions are counted to determine degradative activity. To determine cell-associated ligand, cell monolayers are washed and incubated at 4C with ice-cold buffer "A" containing 150 mM NaCl, 50 mM Tris-HCl, and 2 mg/ml BSA, pH 7.4, to eliminate nonspecifically bound counts. Cells are washed three times rapidly with 1 ml, incubated twice for 10 min each on a rotary shaker in 1 ml buffer A, then washed twice rapidly in 1 ml buffer A without BSA. After aspiration of all wash buffer, cells are lysed in 0.1N NaOH and removed to counting vials for determination of binding/uptake and subsequent protein determination (Pierce BCA protein assay). The present actives yield $IC_{50}$ values of <50 urn in degradation assays and <100 um in binding/uptake assays.

The fluorescent compound DiI-AcLDL (1,1'-dioctadecyl-3,3,3,3'-tetramethylindocarbocyanine perchlorate-labeled LDL) has also been shown to be a useful tool in assessing activity of the macrophage scavenger receptor (Freeman et al., *Proc. Natl. Acad. Sci., USA*, 88:4931–4935 (1991); Penman et al., *J. Biol. Chem.*, 266:23985–23993 (1991)). We also utilized an assay for MSR antagonists based on the uptake of DiI-AcLDL by the transfected HEK 293 cells. For most assays. HEK 293 cells transfected with SR-AI were used, although both SR-AI and SR-AII appeared to have equivalent activity in all studies performed. Briefly, HEK 293 cells were seeded at $2 \times 10^4$ cells/ well in a 96 well plate in EMEM with 2 mM glutamine, 10% FBS and 0.4 mg/ml geneticin. The assay was standardized and optimized, and testing was performed in serum-free EMEM containing 2 mg/ml bovine serum albumin. Confluent cells were incubated with DiI-AcLDL (final concentration 2 ug/ml) in the absence and presence of inhibitors (quadruplicate wells) for 4 hours at 37 C. Following aspiration of solution and a Locke's buffer wash, results were quantified with a fluorescence plate reader at 530 nm exc/590 nm em.

All publications, including but not limited to patents and patent applications cited in this specification are herein incorporated by reference as if each individual publication were specifically and individually indicated to be incorporated by reference as though fully set forth.

What is claimed is:

1. A method of treating a cardiovascular disease or condition which comprises administering to a subject in need of treatment an effective amount of a compound selected from Formula (I) hereinbelow:

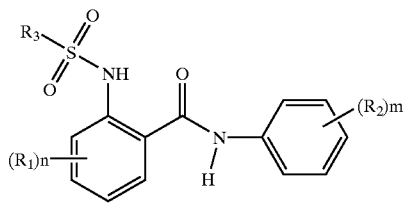

(I)

wherein:

$R_1$ and $R_2$ are independently selected from the group consisting of hydrogen, alkyl, alkenyl, arylalkyl, acyl, aroyl, haloalkyl, halo, carboxy, carboalkoxy, carbamyl, alkylcarbamyl, arylcarbamyl, cyano, alkoxy, hydroxyl, phenylazo, amino, nitro, alkylamino, arylamino, arylalkylamino, acylamino, aroylamino, alkylthio, arylalkylthio, arylthio, alkysulfinyl, arylsulfinyl, arylalkylsulfinyl, alkylsulfonyl, arylsulfonyl, arylalkylsulfonyl, sulfamyl, arylsulfonamido, and alkylsulfonamido;

or the $R_1$ moiety represents a fused ring forming a benzothiophene, naphthalene, quinoline, or isoquinoline with the ring it substitutes;

or $(R_1)_n$ and the ring it substitutes represents a heterocycle selected from the group consisting of thiophene, furan, pyridine, pyrimidine, and pyrazine, and benzo analogs thereof; and $R_3$ is independently selected from the group consisting of alkyl, haloalkyl, $R_1$ aryl and $R_1$ aralkyl, and $R_1$ substituted heterocycles selected from the group consisting of thiophene, furan, pyridine, pyrimidine, pyrazine, imidazole, and thiazole, and benzo analogs thereof.

2. A method according to claim 1 wherein the disease or disorder is selected from the group consisting of atherosclerosis, coronary artery disease, renal disease, thrombosis, transient ischemia due to clotting, organ transplant, organ failure, stroke, myocardial infarction and hypercholesterolemia.

3. A method according to claim 2 wherein the disease or disorder being treated is atherosclerosis.

4. A method of antagonizing a macrophage scavenger receptor comprising administering to a subject in need of treatment an effective amount of a compound selected from the group consisting of:

N-Phenyl-2-(3-trifluoromethylphenylsulfonamido) benzamide,

5-Bromo-N-(3,4-dichlorophenyl)-2-(3-trifluoromethylphenylsulfonamido)benzamide,

N-(4-Chlorophenyl)-2-(2-fluorophenylsulfonamido) benzamide,

5-Bromo-N-(3-trifluoromethylphenyl)-2-(5-chloro-2-thienylsulfonamido)benzamide,

5-Chloro-N-(4-chlorophenyl)-2-(5-chloro-2-thienylsulfonamido)benzamide,

N-(3-Chloro-4-methoxyphenyl)-2-(4-methoxyphenylsulfonamido)benzamide,

N-Phenyl-2-(2-fluorophenylsulfonamido)benzamide,

N-(4-Chlorophenyl)-2-(3-trifluoromethylphenylsulfonamido)benzamide,

N-Phenyl-2-(4-methoxyphenylsulfonamido)benzamide,

N-(4-Chlorophenyl)-2-(3-trifluoromethylphenylsulfonamido)-4-methoxybenzamide,

N-(3-Chloro-4-methoxyphenyl)-2-(3-trifluoromethylphenylsulfonamido)-4-methoxybenzamide, N-(3,4-Dichlorophenyl)-2-(2-fluorophenylsulfonamido)-5-methoxybenzamide, N-(4-Chlorophenyl)-2-(3-trifluoromethylphenylsulfonamido)-5-methoxybenzamide, 5-Chloro-N-(4-chlorophenyl)-2-(4-chlorophenylsulfonamido)benzamide, 5-Chloro-N-(4-chlorophenyl)-2-(3,3,3-trifluoroethylsulfonamido)benzamide, N-(3,4-Dichlorophenyl)-2-(2-phenylsulfonamido)-5-methoxybenzamide, 2-(4-Chlorophenylsulfonamido)-N-(4-ethoxycarbonylphenyl)benzamide, 5-Bromo-N-phenyl-2-(2-fluorophenylsulfonamido) benzamide,
5-Bromo-N-phenyl-2-phenylsulfonamidobenzamide,
5-Bromo-N-phenyl-2-(5-chloro-2-thienylsulfonamido) benzamide,
5-Bromo-N-(4-chlorophenyl)-2-(5-chloro-2-thienylsulfonamido)benzamide,
5-Bromo-N-phenyl-2-(4-methoxyphenylsulfonamido) benzamide,
5-Bromo-N-(4-chlorophenyl)-2-(2-fluorophenylsulfonamido)benzamide,
5-Bromo-N-(4-bromophenyl)-2-(4-nitrophenylsulfonamido)benzamide,
5-Bromo-N-(4-bromophenyl)-2-(5-dimethylamino-1-naphthylsulfonamido)benzamide,
5-Bromo-N-(4-bromophenyl)-2-(phenylsulfonamido) benzamide,
5-Bromo-N-(4-bromophenyl)-2-(3,4-difluorophenylsulfonamido)benzamide,
5-Bromo-N-(4-bromophenyl)-2-(3-trifluoromethylphenylsulfonamido)benzamide,
5-Bromo-N-(4-bromophenyl)-2-(n-butylsulfonamido) benzamide,
5-Bromo-N-(4-bromophenyl)-2-(benzylsulfonamido) benzamide,
5-Bromo-N-(4-bromophenyl)-2-(8-isoquinoylsulfonamido)benzamide,
5-Bromo-N-(4-bromophenyl)-2-(2-fluorophenylsulfonamido)benzamide,
5-Bromo-N-(4-bromophenyl)-2-(2,1,3-benzothiadiazol-4-ylsulfonamido)benzamide,
5-Bromo-N-(4-bromophenyl)-2-(4-chlorophenylsulfonamido)benzamide,
5-Bromo-N-(4-bromophenyl)-2-(3-chloro-4-fluorophenylsulfonamido)benzamide,
5-Bromo-N-(4-bromophenyl)-2-(3-chloro-2-methylphenylsulfonamido)benzamide,
5-Bromo-N-(4-bromophenyl)-2-(2,4,6-trimethylphenylsulfonamido)benzamide,
5-Bromo-N-(4-bromophenyl)-2-(4-iodophenylsulfonamido)benzamide,
N-(4-Bromophenyl)-5-chloro-2-(4-trifluomethoxyphenylsulfonamido)benzamide,
5-Bromo-N-(3-trifluoromethylphenyl)-2-(3-trifluoromethylphenylsulfonamido)benzamide,
5-Bromo-N-(4-bromophenyl)-2-(3,4-dimethoxyphenylsulfonamido)benzamide,
5-Bromo-N-(4-bromophenyl)-2-(4-phenylazophenylsulfonamido)benzamide,
5-Bromo-N-(4-bromophenyl)-2-(2-methylphenylsulfonamido)benzamide,
5-Bromo-N-(4-bromophenyl)-2-(2-naphthylsulfonamido) benzamide,
5-Bromo-N-(4-bromophenyl)-2-(4-phenylphenylsulfonamido)benzamide,
5-Bromo-N-(4-bromophenyl)-2-(2-phenylvinylsulfonamido)benzamide,
5-Bromo-N-(4-bromophenyl)-2-(3-chloropropylsulfonamido)benzamide, and
5-Bromo-N-(4-bromophenyl)-2-(4-t-butylphenylsulfonamido)benzamide.

5. A method of inhibiting lipid accumulation within macrophage-derived foam cells by administering to a subject in need of treatment an effective amount of a compound selected from the group consisting of:
N-Phenyl-2-(3-trifluoromethylphenylsulfonamido) benzamide,
5-Bromo-N-(3,4-dichlorophenyl)-2-(3-trifluoromethylphenylsulfonamido)benzamide,
N-(4-Chlorophenyl)-2-(2-fluorophenylsulfonamido) benzamide,
5-Bromo-N-(3-trifluoromethylphenyl)-2-(5-chloro-2-thienylsulfonamido)benzamide,
5-Chloro-N-(4-chlorophenyl)-2-(5-chloro-2-thienylsulfonamido)benzamide,
N-(3-Chloro-4-methoxyphenyl)-2-(4-methoxyphenylsulfonamido)benzamide,
N-Phenyl-2-(2-fluorophenylsulfonamido)benzamide,
N-(4-Chlorophenyl)-2-(3-trifluoromethylphenylsulfonamido)benzamide,
N-Phenyl-2-(4-methoxyphenylsulfonamido)benzamide,
N-(4-Chlorophenyl)-2-(3-trifluoromethylphenylsulfonamido)-4-methoxy-benzamide,
N-(3-Chloro-4-methoxyphenyl)-2-(3-trifluoromethylphenylsulfonamido)-4-methoxy-benzamide,
N-(3,4-Dichlorophenyl)-2-(2-fluorophenylsulfonamido)-5-methoxybenzamide,
N-(4-Chlorophenyl)-2-(3-trifluoromethylphenylsulfonamido)-5-methoxybenzamide,
5-Chloro-N-(4-chlorophenyl)-2-(4-chlorophenylsulfonamido)benzamide,
5-Chloro-N-(4-chlorophenyl)-2-(3,3,3-trifluoroethylsulfonamido)benzamide,
N-(3,4-Dichlorophenyl)-2-(2-phenylsulfonamido)-5-methoxybenzamide,
2-(4-Chlorophenylsulfonamido)-N-(4-ethoxycarbonylphenyl)benzamide,
5-Bromo-N-phenyl-2-(2-fluorophenylsulfonamido) benzamide,
5-Bromo-N-phenyl-2-phenylsulfonamidobenzamide,
5-Bromo-N-phenyl-2-(5-chloro-2-thienylsulfonamido) benzamide,
5-Bromo-N-(4-chlorophenyl )-2-(5-chloro-2-thienylsulfonamido )benzamide,
5-Bromo-N-phenyl-2-(4-methoxyphenylsulfonamido) benzamide,
5-Bromo-N-(4-chlorophenyl)-2-(2-fluorophenylsulfonamido)benzamide,
5-Bromo-N-(4-bromophenyl)-2-(4-nitrophenylsulfonamido)benzamide,
5-Bromo-N-(4-bromophenyl)-2-(5-dimethylamino-1-naphthylsulfonamido)benzamide,
5-Bromo-N-(4-bromophenyl)-2-(phenylsulfonamido) benzamide,
5-Bromo-N-(4-bromophenyl)-2-(3,4-difluorophenylsulfonamido)benzamide,
5-Bromo-N-(4-bromophenyl)-2-(3-trifluoromethylphenylsulfonamido)benzamide,
5-Bromo-N-(4-bromophenyl)-2-(n-butylsulfonamido) benzamide, 5-Bromo-N-(4-bromophenyl)-2-(benzylsulfonamido)benzamide, 5-Bromo-N-(4-bromophenyl)-2-(8-isoquinoylsulfonamido)benzamide, 5-Bromo-N-(4-bromophenyl)-2-(2-fluorophenylsulfonamido)benzamide, 5-Bromo-N-(4-bromophenyl)-2-(2,1,3-benzothiadiazol-4-ylsulfonamido)benzamide, 5-Bromo-N-(4-bromophenyl)-2-(4-chlorophenylsulfonamido)benzamide, 5-Bromo-N-(4-bromophenyl)-2-(3-chloro-4-fluorophenylsulfonamido)benzamide, 5-Bromo-N-(4-bromophenyl)-2-(3-chloro-2-methylphenylsulfonamido)benzamide, 5-Bromo-N-(4-bromophenyl)-2-(2,4,6-trimethylphenylsulfonamido)benzamide, 5-Bromo-N-(4-bromophenyl)-2-(4-iodophenylsulfonamido)benzamide, N-(4-Bromophonyl)-5-chloro-2-(4-trifluomethoxyphenylsulfonamido)benzamide, 5-Bromo-N-(3-trifluoromethylphenyl)-2-(3-trifluoromethylphenylsulfonamido)benzamide, 5-Bromo-N-(4-bromophenyl)-2-(3,4-dimethoxyphenylsulfonamido)benzamide, 5-Bromo-N-(4-bromophenyl)-2-(4-phenylazophenylsulfonamido)benzamide, 5-Bromo-N-(4-bromophenyl)-2-(2-methylphenylsulfonamido)benzamide, 5-Bromo-N-(4-bromophenyl)-2-(2-naphthylsulfonamido)benzamide, 5-Bromo-N-(4-bromophenyl)-2-(4-phenylphenylsulfonamido)benzamide, 5-Bromo-N-(4-bromophenyl)-2-(2-phenylvinylsulfonamido)benzamide, 5-Bromo-N-(4-bromophenyl)-2-(3-chloropropylsulfonamido)benzamide, and 5-Bromo-N-(4-bromophenyl)-2-(4-t-butylphenylsulfonamido)benzamide.

* * * * *